United States Patent [19]
Miller

[11] 4,080,970
[45] Mar. 28, 1978

[54] POST-OPERATIVE COMBINATION DRESSING AND INTERNAL DRAIN TUBE WITH EXTERNAL SHIELD AND TUBE CONNECTOR

[76] Inventor: Thomas J. Miller, 800 Lombard Ave., Evansville, Ind. 47715

[21] Appl. No.: 742,612

[22] Filed: Nov. 17, 1976

[51] Int. Cl.² ............................................. A61M 27/00
[52] U.S. Cl. .................................. 128/350 R; 128/245
[58] Field of Search ............................ 128/348–351, 128/239, 241, 245, 248, 283, 155, DIG. 26

[56] References Cited

U.S. PATENT DOCUMENTS

| | | | |
|---|---|---|---|
| 989,839 | 4/1911 | Fowler | 128/248 |
| 1,188,180 | 6/1916 | Kells | 128/350 R |
| 2,679,248 | 5/1954 | Fullaway | 128/283 |
| 3,422,817 | 1/1969 | Mishkin et al. | 128/DIG. 26 |
| 3,895,629 | 7/1975 | Snyder | 128/DIG. 26 |

*Primary Examiner*—Dalton L. Truluck
*Attorney, Agent, or Firm*—Laurence R. Brown

[57] ABSTRACT

The invention is a novel drainage tube system, to be used following surgery, where drainage is necessary. It comprises a protective shield of spherical segmental configuration, having a recessed flat surface on one side and a spherical surface on the other side. In a modification, the flat surface is omitted and the spherical segment is open. An internal drainage tube penetrates the shield and terminates externally thereof on the spherical side in tube connector means comprising a bulbous portion spaced from the spherical side of the shield and a threaded portion intermediate the bulbous portion and spherical side. This enables fluid-tight connection with the internal tube for the external drainage tube sufficient even for the application of a pump, if necessary, but admitting of ready removal for inspection or patient transfer. Gauze or other absorbent dressing material, conforming in configuration to the bottom side of the shield, includes a central opening to accommodate the internal tube and a split from the opening to the edge to facilitate dressing application and change. The dressing is held in place against the body by the shield, in turn taped firmly in place to anchor the tubes and protect the opening while maintaining the dressing intact. The apparatus may be assembled or pre-cast integrally, as a disposable kit, from soft, flexible material.

6 Claims, 3 Drawing Figures

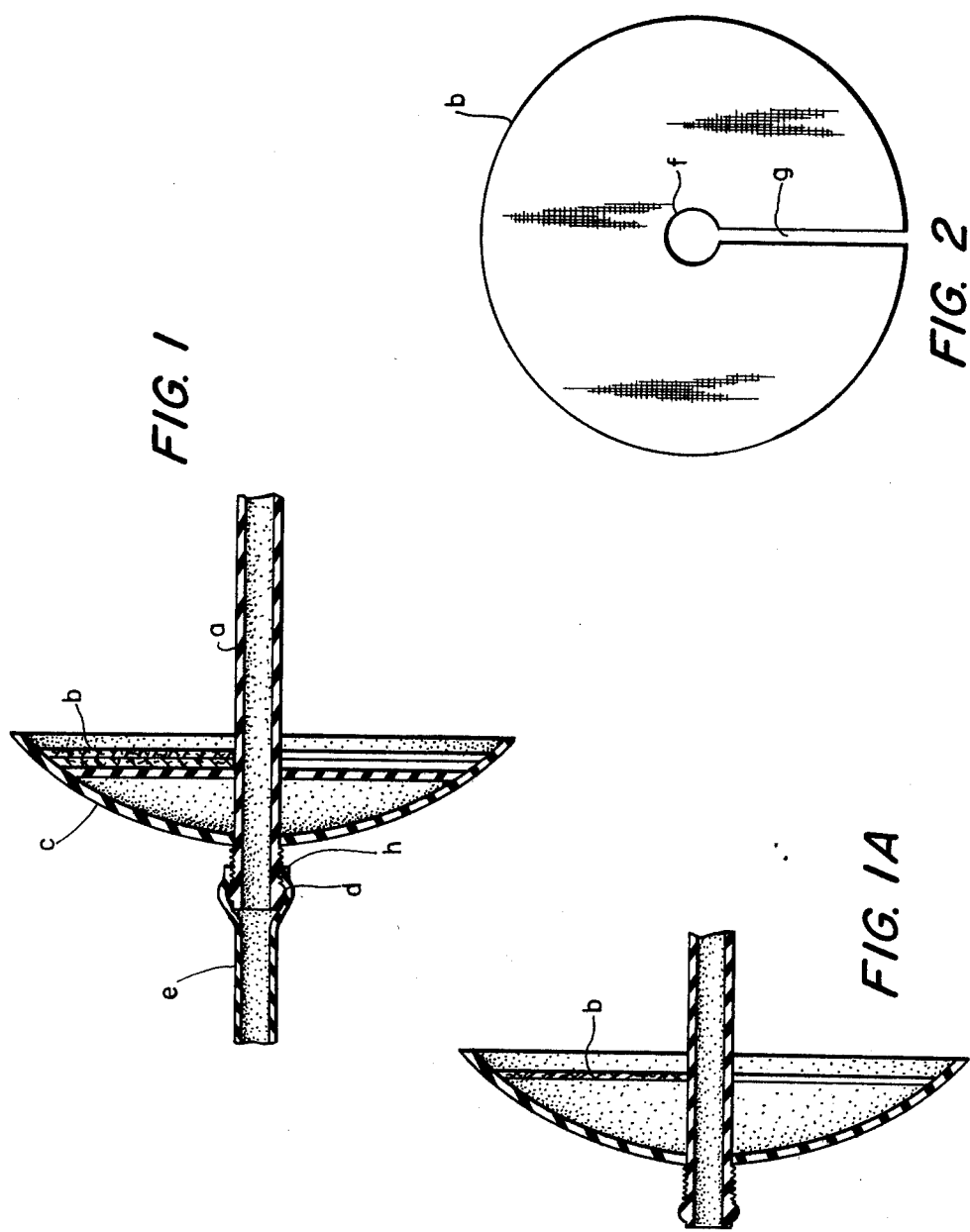

POST-OPERATIVE COMBINATION DRESSING AND INTERNAL DRAIN TUBE WITH EXTERNAL SHIELD AND TUBE CONNECTOR

BACKGROUND OF THE INVENTION

Many problems are encountered when it is necessary to drain a body through a surgical opening following surgery. It will be appreciated that the patient is usually experiencing discomfort and consequently changes position frequently. The presence of drainage apparatus is likely to aggravate the wound, even to the point of tearing it, or at least gaping it open, to the extent of enlarging the opening and attendant scar tissue. Also, other problems exist when it is necessary to apply a pump to assist drainage or to inspect the drainage site or to change the dressing material, and it is the solution to these many problems to which the present invention is oriented.

PRIOR ART

The prior art is cumbersome, at best, and does not accomplish the many functions attributable to the present invention. For example, in the U.S. Pat. to Solomon, No. 2,606,555, a bridge type holder for a surgical tube or drain incorporates a valve. The bridge stands between spaced apart base portions to accommodate a gauze pad which is penetrated by a rubber drain tube, in turn held in place by tape, which anchors the bridge to the body after the dressing is in place. The configuration is awkward and not compatible to body configuration and retention.

The present invention improves over the prior art by providing an assemblable or an integrally cast post-operative apparatus which protects the body surgical opening, while draining fluid from the body, and maintaining changeable dressing material in place. It comprises a shield which may be described as cup-shaped, dome-shaped or pictured as a closed spherical segmented configuration having a flat surface on one side and a spherical surface on the opposite side. The flat side is adapted to cover a conforming gauze or other absorbent dressing material (one or more) against the body, with the shield offering minimum edges or surfaces for dislodgement. The flat surface is slightly recessed upward from the bottom edge of the shield to allow dressing to be enclosed by the circular rim of the bottom of the shield. An alternate shield may be pictured as a spherical segmented configuration having a spherical side and an open bottom. The open bottom is adapted to enclose and hold a conforming gauze or other absorbent material (one or more) in position against the body without creating undue pressure.

An internal drain tube penetrates the shield and terminates in an external tube connector means on the spherical side of the shield. The connector means comprises a bulbous portion spaced apart from the spherical side with a threaded portion intermediate the bulbous portion and spherical side. This provides a sufficient seal for even enabling a pump to assist in drainage when necessary. However, it also provides a quick connect-disconnect terminal between the internal and external tubes.

One or more dressings is adapted to be configurated in the shape of the bottom part of the shield. Both the shield and the dressings include a central circular opening sized to the diameter of the internal tube, for snug fitting thereabout; with a slit or split extending from the central opening of the dressing to the dressing edge to facilitate insertion and removal of each dressing.

The material of the apparatus is soft rubber or soft plastic and it may comprise an assembled apparatus or an integrally cast throw-away post-operative surgical kit.

In operation the sterile internal tube is carefully inserted into the surgical opening. In the case of integral units, several sizes are available as to internal tube length and diameter, in order that the surgeon merely chooses the proper size. Otherwise, of course, the internal tube may be adjusted relative to the shield to limit the tubing inserted into the body.

One or more gauze dressings are slipped over the internal tube, with the shield then being placed over the dressing against the body and taped firmly to anchor the dressing and protect the opening while providing drainage access. Normally, an external tube would be engaged at the external tube connector means to complete the procedure.

Whenever it is desirable or necessary to change the dressing, the shield is untaped and removed just a slight distance from the body to permit withdrawal of the used dressings and insertion of new dressings with a minimum of disturbance to the body opening and interior. The dressings are then pressed firmly against the body and the shield retaped to complete this procedure. Also, the quick disconnect external tube connector means enables ready observation at any time of the discharge in the vicinity of the shield.

It may now be appreciated that the invention provides an improved drainage tube system with a sterile internal extension of a surgical drain tube. The contour of the shield makes it much more difficult for the patient to interfere with its anchoring function or to pull the drainage tube out of the body.

Another feature of the ready disconnect structure is to make it easy to disconnect the outer drain tube when it becomes necessary to move the patient or for any other reason.

In performing its provision of a sterile package used as a post-operative combination dressing and drainage tube with shield, it will be appreciated that fitting the dressing over the tube and removing the dressing is conveniently accomplished with the requisite function of the dressing to prevent leakage and guard against infection being conveniently accomplished, also.

Finally an important object of the invention is realized through the ready disconnect structure when the patient is being weaned from the drainage tube. The external tube may be removed for various lengths of time to determine the necessity of further drainage, leaving the internal tubing in place until it is determined that the drainage tube can be removed altogether. This may require removing the internal tube only once, thereby allowing for faster healing and less disturbance of the drainage hole.

The invention will be better understood from a reading of the following detailed description thereof when taken in light of the accompanying drawing wherein:

FIG. 1 is a view in cross section of the complete assembly or cast structure of the present invention, showing the flat recessed bottom of the shield;

FIG. 1-A is a view in cross section showing an alternate shield with open bottom; and, FIG. 2 is a view in elevation or top plan of a typical gauze dressing for use in the apparatus of FIGS. 1 and 1-A.

In FIG. 1, the internal tube a, is shown centrally penetrating the shield c, the shield c comprising, preferably, a closed spherical segment taken from a hollow sphere to provide a streamline surface to avoid dislodgement. Both the internal tube a, and shield c, are sectioned for rubber, but they may also comprise soft plastic, as previously mentioned.

FIG. 1-A is similar to FIG. 1 except it comprises an open spherical segment taken from a hollow sphere to provide a streamlined surface to avoid dislodgement. It will accommodate extra dressing b, although only a single layer is illustrated.

The preferred gauze dressing b, is shown in FIG. 3, having a central opening f, conforming to the central opening, which openings are both adapted to fit snugly about the internal tube a. FIG. 1 includes two layers of dressing b.

Opening f, of gauze dressing b, communicates with slot g, extending to the outer peripheral edge of dressing b, in order that this dressing may be slipped over internal tube a, without requiring disassembly of shield c and tube a, and without requiring extraction of tube a, but merely a slight displacement of shield c from against the body to enable replacing dressing b.

In order to provide a quick connect-disconnect junction between internal drain tube a and the external drain tubing e, a bulbous portion d, is formed about the perimeter of internal drain tube a, and a threaded portion h, is provided intermediate bulbous portion d and the spherical surface of shield c, whereby a seal sufficient for a drainage pump is quickly enabled as a result of the portion d, stretching the internal periphery of the external drain tube and the threads of threaded portion h, frictionally engaging the end of the external drain tube.

As previously discussed, the invention may be assembled by sliding internal drain tube a, variable lengths through shield c, or the parts a, c, d and h may be integrally cast readily to accommodate dressing b, for disposable use.

It may now be appreciated that the subject invention has been simplified to an extent emphasizing reliability while incorporating a large number of functions, some of which have not heretofor been available. It is the economy which permits the disposable kit approach.

What is claimed is:

1. Post-operative combination apparatus for protecting a body surgical opening while draining fluid from the body and maintaining changeable dressing material in place over the opening comprising,
  a shield of spherical segmented configuration having a spherical surface on one side;
  an internal drain tube for insertion into the body via the surgical opening at one end which penetrates the shield adjacent the other end;
  external tube connector means carried on said other end of the internal tube beyond the spherical side of the shield; and,
  dressing material of a configuration to conform to the shield substantially opposite said one side and further including a central opening to accommodate the internal tube and a split from the central opening to the outer edge of the material to permit seating the material on the internal tube adjacent the opposite side thereof shield for sealing the opening when the shield is taped tightly to the body with the dressing material interposed between the body and the bottom part thereof wherein said external tube connector means comprises, a peripheral bulbous portion spaced from the spherical side of said shield; and, a threaded portion between said bulbous portion and said spherical side of the shield.

2. The apparatus of claim 1 wherein, said internal tube, said shield, and said external tube connector means are integral to comprise a post-operative throwaway kit, and the opposite side open.

3. The apparatus kit of claim 2 wherein, said internal tube, said shield, and said external tube connector are all comprised of the same flexible soft material cast into the claimed configuration.

4. Post-operative combination apparatus for protecting a body surgical opening while draining fluid from the body and maintaining changeable dressing material in place over the opening comprising,
  a spherical shield;
  an internal drain tube for insertion into the body via the surgical opening at one end and having its other end extending through the shield;
  external tube connector means carried on said other end of the internal tube beyond the shield; and,
  dressing material configured to conform to the shield, including a central opening to accommodate the internal tube and a split from the central opening to the outer edge of the material, seated on the internal tube for sealing against leakage when the shield is taped tightly to the body, with the dressing material interposed between the body and the shield wherein said external tube connector means comprises, a peripheral bulbous portion about the other end of the internal drain tube, spaced from the spherical side of said shield and, a threaded portion of the external periphery of the internal drain tube between said bulbous portion and said spherical side of the shield.

5. The apparatus of claim 4 wherein, said internal tube, said shield, and said external tube connector means are integral to comprise a post-operative throwaway kit.

6. The apparatus kit of claim 5 wherein, said internal tube, said shield, and said external tube connector means are all comprised of the same flexible soft material cast into the claimed configuration.

* * * * *